(12) United States Patent
Akerfeldt et al.

(10) Patent No.: US 6,425,911 B1
(45) Date of Patent: Jul. 30, 2002

(54) POSITIONING DEVICE AND INCISION CLOSURE DEVICE

(75) Inventors: Dan Akerfeldt; Fredrik Preinitz; Per Egnelov, all of Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 09/864,919

(22) Filed: May 25, 2001

(30) Foreign Application Priority Data

May 9, 2001 (EP) .............................. 01111086

(51) Int. Cl.$^7$ .............................. A61B 17/03
(52) U.S. Cl. ...................... 606/213; 606/215
(58) Field of Search ............... 606/213, 215, 606/216, 217, 218, 157, 158

(56) References Cited

U.S. PATENT DOCUMENTS

| | | | |
|---|---|---|---|
| 4,852,568 A | 8/1989 | Kensey | 128/325 |
| 4,890,612 A | 1/1990 | Kensey | 606/213 |
| 4,917,089 A | 4/1990 | Sideris | 606/215 |
| 5,053,046 A | 10/1991 | Janese | 606/215 |
| 5,342,393 A * | 8/1994 | Stack | 24/453 |
| 5,350,399 A | 9/1994 | Erlebacher et al. | 606/213 |
| 5,501,700 A * | 3/1996 | Hirata | 606/151 |
| 5,853,422 A * | 12/1998 | Huebsch et al. | 606/213 |
| 5,904,703 A * | 5/1999 | Gilson | 606/213 |

* cited by examiner

Primary Examiner—Ismael Izaguirre
(74) Attorney, Agent, or Firm—Foley & Lardner

(57) ABSTRACT

A positioning device comprises a rod-shaped portion which in its distal end, is releasable attachable to said first sealing member such that a rotational movement and a directional movement of the rod-shaped portion are transferable to the first sealing member, which makes the positioning of said first sealing member controllable and the way of sealing improved and more secure.

23 Claims, 5 Drawing Sheets

POSITIONING DEVICE AND INCISION CLOSURE DEVICE

FIELD OF THE INVENTION

The present invention relates to a positioning device and an incision closure device according to the preamble of claims 1 and 23, respectively.

BACKGROUND

During certain types of medical surgery or treatment an introducer is used to access the vascular system of a patient. The introducer is inserted through the wall of a blood vessel in order to obtain access to the vascular system and may thereafter be used for guiding medical instruments such as catheters, guide wires and the like.

After the completion of the medical procedure there will be an incision or a wound in the wall of the blood vessel corresponding to the size of the introducer. The bleeding from the incision, which is the result of such a surgical operation, may be stopped by applying direct pressure on the incision. However, applying direct pressure on the incision will require assistance of medical personnel and may also restrict the blood flow through the vessel.

U.S. Pat. No. 5,350,399 describes a sealing device for sealing an opening in a vessel. The sealing device is constructed of an absorbable member in the form of an intra-arterial occluder, a guide means in the form of an elongated absorbable wire integral with and extending centrally from the intra-arterial occluder and a second absorbable member in the form of an extra-arterial occluder.

A problem with such a sealing device is that it is difficult to position the intra-arterial occluder at the moment before the sealing, since there is a risk that the force of blood flow moves the intra-arterial occluder so that it gets stuck crossways in the vessel, and thus it is hard to know if the sealing device is properly sealed or not. This may have disastrous consequences with blood leaking vessels. The rate of the blood flow is approximately 0.5 m/s.

SUMMARY OF THE INVENTION

The object of the present invention is to provide a positioning device for positioning a sealing device that makes the way of sealing improved and more secure.

This problem is solved by the invention according to the features of the independent claims 1 and 23.

The positioning device comprises a rod-shaped portion which in its distal end, is releasable attachable to said first sealing member such that a rotational movement and a directional movement of the rod-shaped portion are transferable to the first sealing member. Thereby the position of said first sealing member can be controlled which makes the way of sealing improved and more secure.

Preferred embodiments of the plug according to the invention are defined in the dependent claims 2–22.

Thus, it is believed that the present invention provides a novel and easy-to-use sealing and incision closure device for closing an incision with excellent sealing properties.

BRIEF DESCRIPTION OF THE DRAWINGS

The foregoing and other aspects of the present invention will be best appreciated with reference to the following detailed description of specific embodiments of the invention, given by way of example only, when read in conjunction with the accompanying drawing, wherein.

DESCRIPTION OF THE PREFERRED EMBODIMENTS

Figure 1:
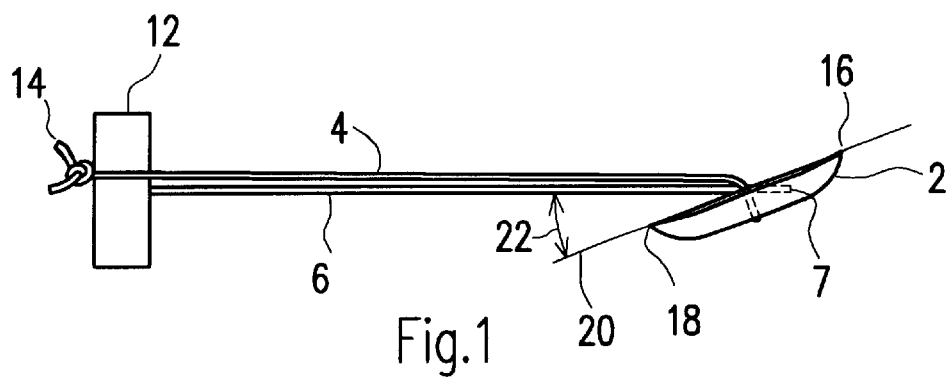
FIG. 1 shows side view of a positioning device positioning a sealing device according to a first embodiment of the present invention.
Figure 2:
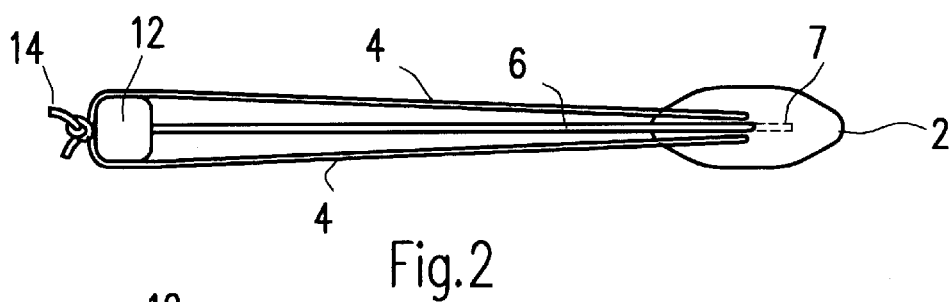
FIG. 2 shows a positioning device positioning a sealing device seen from above, according to a first embodiment of the present invention.
Figure 6:
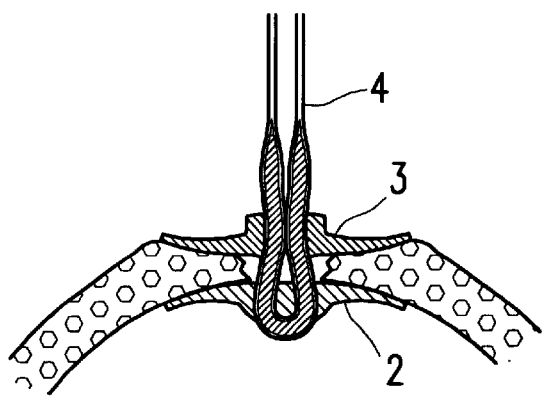
FIG. 6 shows an example of a sealing device that can be positioned by the positioning device according to the present invention.

FIG. 1 shows a side view and FIG. 2 a view seen from above, of a positioning device attached for positioning of a sealing device according to a first embodiment of the invention. The sealing device is intended for closing an incision in a wall of a vessel and an example of such a sealing device is shown in its sealed position in FIG. 6. It comprises three separate parts, namely a first sealing member 2, an elongated member and a second sealing member 3. The first sealing member 2 is attached to a distal end of the elongated member. The elongated member is made of a shapeless material, such as multifilament suture wire. In this example, the first sealing member comprises two through openings, through which the multifilament suture wire is threaded so as to make a pair of suture wires 4, which constitutes the elongated member. The second sealing member 3 comprises a through opening through which the suture wires 4 is threadable such that the second sealing member can be brought to its sealing position.

Referring to FIG. 1 and FIG. 2, the positioning device comprises a rod-shaped portion 6, which in its distal end is attachable to the first sealing member 2. According to the first embodiment, the rod-shaped portion 6 in its distal end fits in a notch 7 in the first sealing member 2 and in this way can be attached to the first sealing member 2 and easily be removed.

Figure 3:
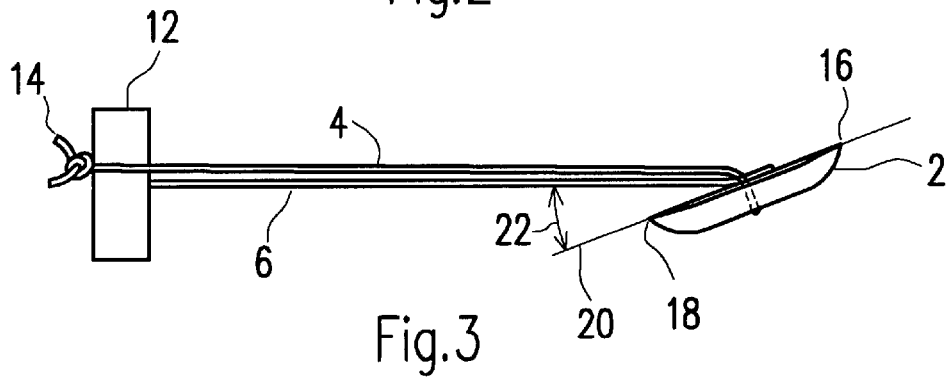
FIG. 3 shows side view of a positioning device positioning a sealing device according to a second embodiment of the present invention.
Figure 4:
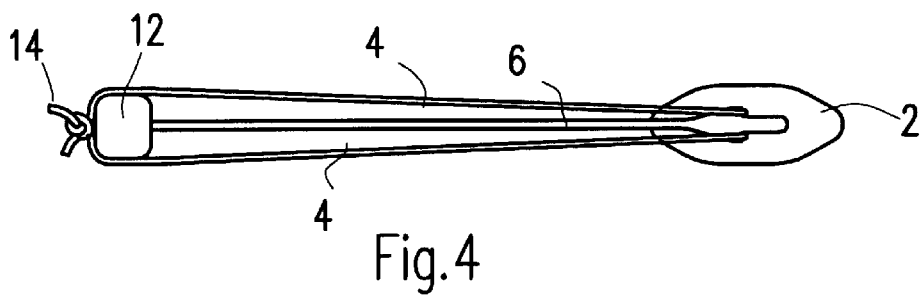
FIG. 4 shows a positioning device positioning a sealing device seen from above, according to a second embodiment of the present invention.
Figure 5:
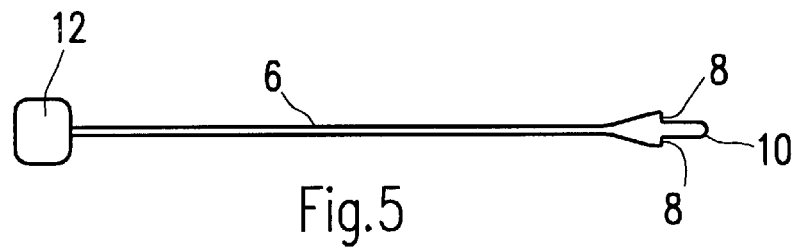
FIG. 5 shows a positioning device seen from above according to a second embodiment of the present invention.

According to a second embodiment, shown in FIGS. 3–5, the rod-shaped portion 6 in its distal end comprises a shoulder 8 on each side of a projecting part 10 so that the rod-shaped portion 6 fits in between the two suture wires extending from the first sealing member 2 and the first sealing member 2 and is in this way attachable to the first sealing member 2 and easily be removed.

Figure 15:
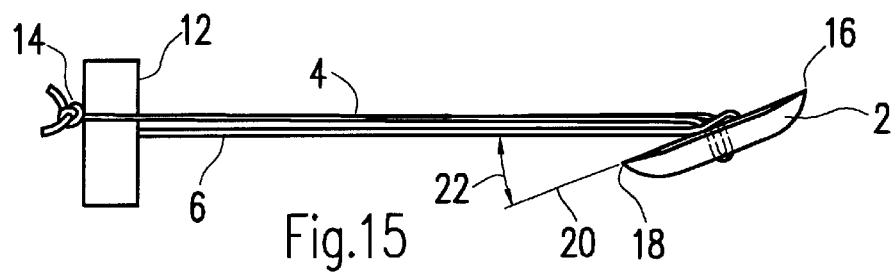
FIG. 15 shows side view of a positioning device positioning a sealing device according to a third embodiment of the present invention.
Figure 16:
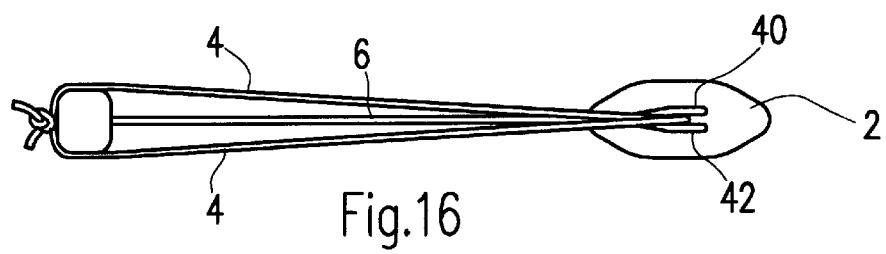
FIG. 16 shows a positioning device positioning a sealing device seen from above, according to a third embodiment of the present invention.
Figure 17:
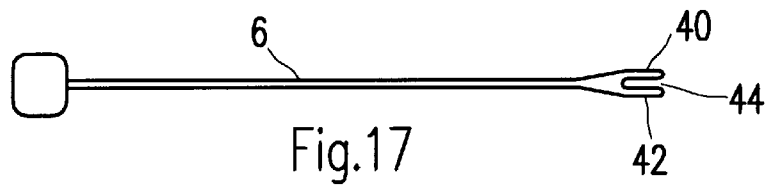
FIG. 17 shows a positioning device seen from above according to a third embodiment of the present invention.

According to a third embodiment, shown in FIGS. 15–17, the rod-shaped portion 6 in its distal end comprises two projecting parts 40 and 42 and a space 44 in-between forming a fork. The fork surrounds the two suture wires 4 extending from the first sealing member 2 and thus, the rod shaped portion 6 is attachable to the first sealing member 2 and is also easily removable.

Figure 18:
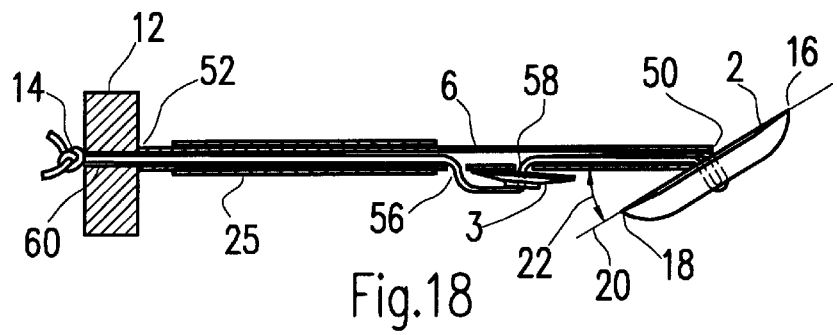
FIG. 18 shows a side view of a positioning device positioning a sealing device according to a fourth embodiment of the present invention.
Figure 19:
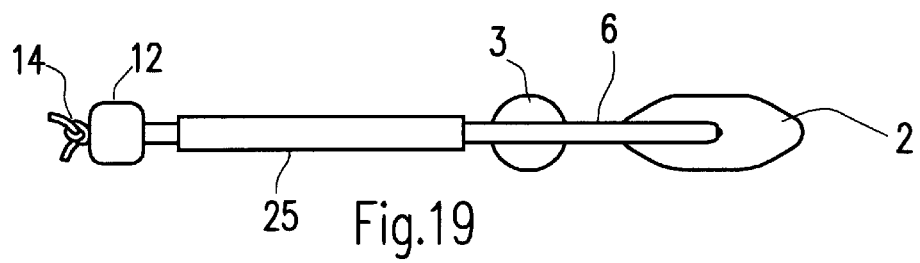
FIG. 19 shows a positioning device positioning a sealing device seen from above, according to a fourth embodiment of the present invention.
Figure 20:
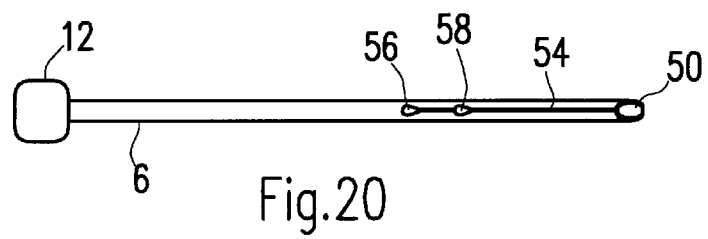
FIG. 20 shows a positioning device seen from above according to a fourth embodiment of the present invention.

According to a fourth embodiment, shown in FIGS. 18–20, the rod-shaped portion 6 is tube formed and has a first opening 50 in its distal end and a second opening 52 in its proximal end. As illustrated in FIG. 20, a part of the tube comprises a longitudinal slit 54 extending from the distal. The slit 54 is terminated in a first opening 56 and includes further a second opening 58 between the first opening 56 and the distal end such that the suture wire 4, extending from the first sealing member 2, is threadable in through the first opening 50 in the rod-shaped portion 6, out through the second opening 58 of the slit, through the through opening of the second sealing member 3, in through the first opening 56 of the slit, and out of the rod-shaped portion through its second opening 52, (see FIG. 18). Consequently, the rod shaped portion 6 is attachable to the first sealing member 2 and is also easily removable. The slit 54 makes it possible to bring the second sealing member 3 to its locking position.

The rod-shaped portion 6 is preferably kept in place in the first sealing member 2 by the elongated member, i.e. in this example the two suture wires 4, by fasten the proximal end of the rod shaped portion 6 in the proximal ends of the suture wires 4 extending from the first sealing member 2. The positioning device may comprise a support 12. The support 12 is attached to or is a part of the proximal end of the rod-shaped portion 6. The proximal end of the elongated member may be fastened to the support 12, so that a pressure appears that tightens the rod-shaped portion 6 to the first sealing member 2 so as to keep them safer together in place. As long as the suture wires 4 are tightened the first sealing member 2 is guidable in all directions. The fastening can be performed e.g. by knotting 14 the proximal ends of the suture wires around the support 12 as hard as the desired pressure appears, as in the first, second and third embodiment of the present invention, see FIG. 2, FIG. 4, and FIG. 16. The fourth embodiment is similar but the support 12 comprises a through opening 60 through which is thread, the suture wires 4 extending from the proximal end of the tube formed rod-shaped portion 6, and knotted on the side opposite to the rod-shaped portion 6, see FIG. 18. The first and second openings 54 and 56 of the slit 54, are preferably drop formed such that the point of the drops point at the distal end of the rod-shaped portion 6. This is advantageous since the suture wires 4 will not slide out of the tube formed rod-shaped portion 6 when the suture wires 4 are tightened and when the first sealing member 2 is forced in through the introducer 24. On the other hand, upon releasing, the suture wires 4 slides out through the rod-shaped portion 6 tube since the first and second openings 54 and 56 continuous changed over to the slit 54.

The elongated member, e.g. the suture wire 4 is releasable from the rod shaped portion 6 of the positioning device, when the positioning device is to be pulled away.

Referring to FIG. 1, FIG. 3 and FIG. 15, the first sealing member 2 comprises a front part 16, which is the part of the first sealing member 2 that first enters trough the incision. The first sealing member 2 comprises further a rear part 18, which is the part of the first sealing member 2 that last enters through the incision. A line 20 is depicted between the front part 16 and rear part 18 in said figures. The angle 22 between the longitudinal axis of the rod-shaped portion 6 and the first sealing member 2, i.e. the line 20, is important for a secure sealing. The angle 22 shall be somewhere between two requirements of the angle 22, when the rod-shaped portion 6 and the first sealing member 2 is in a sealing position. The first is that it shall be as small as the line 20 is parallel to the blood vessel. The second requirement of the angle 22 is that it shall be as large as there is no risk that the second sealing member 2 is pulled out of the vessel when the elongated member e.g. the suture wire 4, tightens, A suggestion of such an angle would be between approximately 15–30°.

To provide the desired angle 22 in the first embodiment (see FIG. 1), the notch 7 in the first sealing member 2 has such an angle so that when the rod-shaped portion 6 is adapted into the notch 7, the desired angle is provided and it is a fixed angle.

To provide the desired angle in the second embodiment (see FIG. 3), the projecting part 10 is bent to the same angle as the desired angle.

To provide the desired angle in the third embodiment the two projecting parts 40 and 42 are bent to slightly the same angle as the desired angle, similar to the second embodiment. Preferably, the tips of the two projecting parts 40 and 42 are further bent such that the distal end of the rod-shaped portion 6 is S-shaped which makes the positioning device smoother in its distal end. (see FIG. 15).

To provide the desired angle in the fourth embodiment (see FIG. 18), the opening 50 of the tubular rod-shaped portion 6 is slanted in the same angle as the desired angle.

Figure 10:
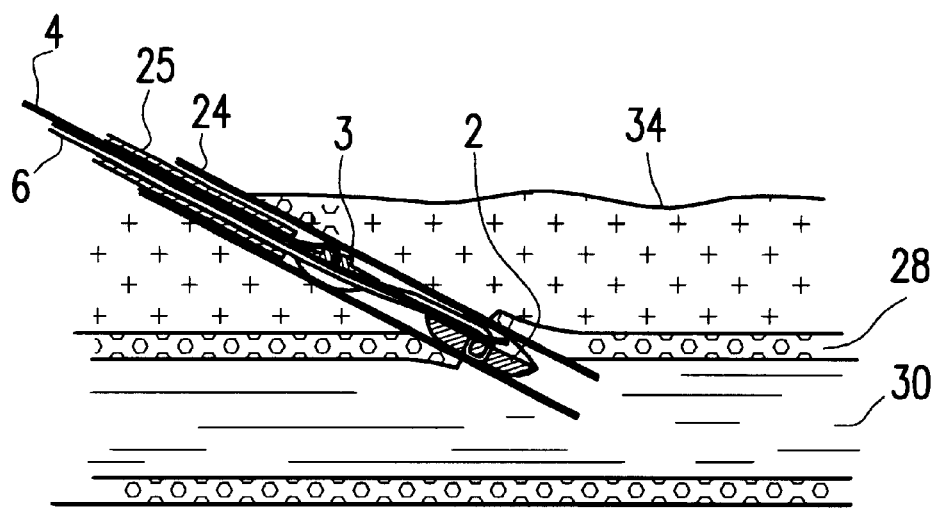
FIG. 10 shows a sectional view of the incision site, with the positioning device, the first sealing member and the elongated member, inside of the introducer.

When the rod-shaped portion 6 is adapted in-between the two suture wires extending from the first sealing member 2 and the first sealing member 2 according to the second and third 10 embodiment, the desired angle is provided. In the second, third and fourth embodiment, the angle is not fixed, the first sealing member 2 can pivot so that the angle 22 is between 0° up to the angle to which the projecting part 10, 40 and 42 is bent according to the second and third embodiment, or up to the angle of which the opening 50 of the tubular rod-shaped portion 6 is slanted to according to the fourth embodiment. In FIG. 10 and FIG. 12, the first sealing member 2 is pivoted so that the angle is 0° and in FIG. 11 the first sealing member 2 is pivoted so that the angle is the desired angle. As it can be seen from FIG. 10, the first sealing member 2 has to be adjusted to the space inside the introducer 24, i.e. the longitudinal axis of the first sealing member 2 representing the line 20 is adjusted to be parallel to the longitudinal axis of he introducer 24. Accordingly the pivot is advantageous since the required power for the positioning device for introducing and deforming the second sealing member 2 is decreased.

The rod-shaped portion 6 is made of a resilient material, preferably having a high e-module, e.g. stainless steel with an e-module of typically 2000 GPa or a polymer having an e-module of typically 200 GPa.

Typical dimensions of the positioning device are, for the rod shaped portion 6 a length of 150 mm and a thickness of 0.4 mm. For the deep of the notch 7 according to the first embodiment, 2 mm. For the shoulders 8, a width of 0.5 mm and for the projecting part 10, a length of 2 mm and a width of 0.5 mm according o the second embodiment of the present invention. For the projecting parts 40 and 42, a length of 2 mm and a width of 0.3 mm according to the third embodiment of the present invention. According to the fourth embodiment of the present invention, the typical dimensions are for the slit 54 a length of 12 mm, the distance from the distal end 50 of the slit to its first opening 56, 7 mm and to its second opening 58 12 mm, the width of the slit openings 56 and 58 a diameter of 0.5 mm.

Typical dimensions of the parts of the sealing device are, for the length of the first sealing member 2 10 mm, for the width of the first sealing member 2 5 mm, for the two through openings of the first sealing member 2, a diameter of 0.2 mm. The typical dimension of the suture is a diameter of 0.25 mm.

The inner diameter of the vessel is 6–10 mm.

Figure 7:
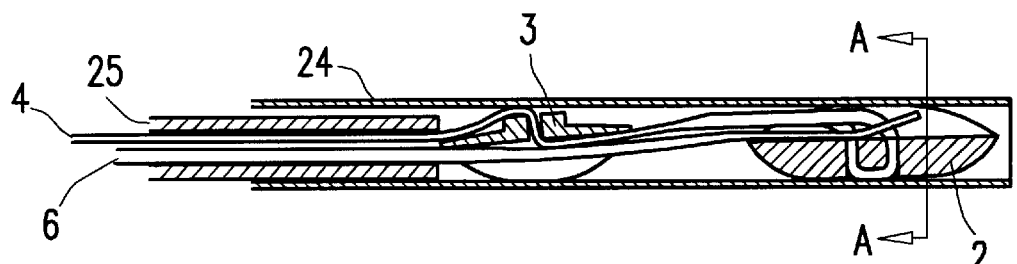
FIG. 7 device according to a second embodiment of the invention.
Figure 8:
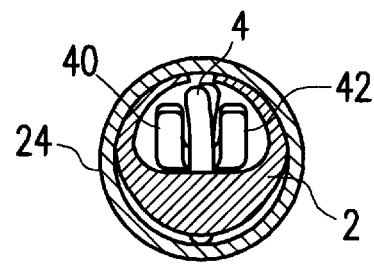
FIG. 8 shows an introducer, which comprises the first sealing member and the positioning shows a cross sectional view of the first sealing member compressed inside the introducer according to FIG. 7, seen along the line A—A.

FIG. 7 shows an introducer, which comprises the first sealing member and the positioning device according to the third embodiment of the present invention. The first and second sealing member 2, 3 will pass through an introducer 24 on the way to its final position in the incision. Since the first and second sealing member 2 and 3, each has a diameter that is greater than the diameter of the introducer 24 they are made compressible. The first and second sealing member 2 and 3, according to the present invention are preferably built up of portions that are foldable and portions that are more rigid, but other shapes are also possible. FIG. 8 shows a cross sectional view of the first sealing member 2 compressed inside the introducer 24 according to FIG. 7, seen along the line A—A.

FIG. 10 shows an introducer, which comprises the sealing device according to the third embodiment of the present invention and the positioning device adapted for pushing and positioning the first sealing member 2, the elongated member and the second sealing member 3 through an introducer 24.

The sealing device will be passed through the introducer 24 in order to reach its final position in the incision to be closed. To achieve this, a tamping tube 25 and the positioning device 6 are used to push the first sealing member 2, the elongated member and the second sealing member 3 through the introducer 24.

It will now be described how the different elements of the introducer, the positioning device and the sealing device operate and their relation to each other.

Figure 9:
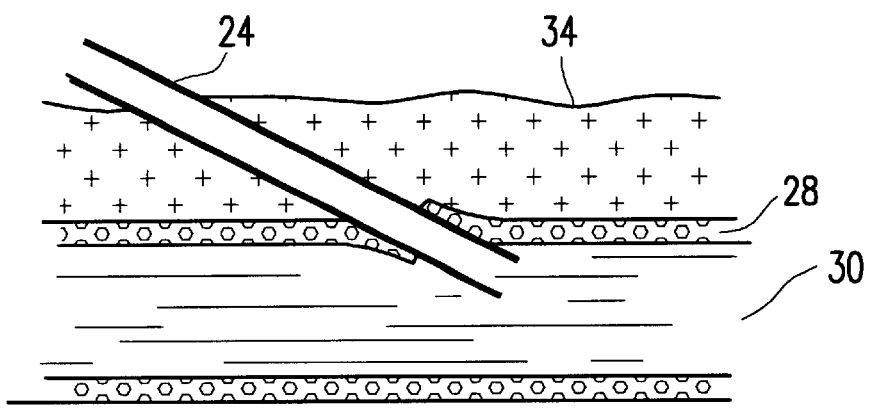
FIG. 9 shows a sectional view of an incision site, with an introducer extending through the vessel wall and into the vessel.

The introducer 24 is used to access the vascular system of a patient. The introducer 24 is inserted through the wall of a blood vessel in order to obtain access to the vascular system and may thereafter be used for guiding medical instruments such as catheters, guide wires and the like. FIG. 9 shows a sectional view of an incision site, with an introducer 24 extending through the vessel wall 28 and into the vessel 30. The introducer 24 is introduced through the skin and passes the tissue 34 before it penetrates the vessel wall 28 and enters the vessel 30. When the introducer 24 is removed, an incision will be left in the vessel wall 28. It is that incision that the sealing device will close, by means of the positioning device described above.

Before the sealing process starts, the rod shaped portion 6 is attached to the first sealing member 2. They are kept together by fastening the proximal end of the elongated member to the support 12 so that a pressure appears that pressures the rod-shaped portion 6 against the first sealing member 2 as described above. The rod shaped portion 6, and the first and second sealing members 2 and 3 are then pressured into the introducer, so that the first and second sealing members 2 and 3 become compressed as shown in FIG. 7 and 8.

FIG. 10 shows a sectional view of the incision site, with the positioning device according to the second or third embodiment, the first and second sealing members 2 and 3, the tampering tube 25 and the elongated member inside the introducer 24. As can be seen in FIG. 10, the positioning device has pushed the first sealing member 2 such that it is situated in the distal end of the introducer 24. The first sealing member 2 is pivoted towards the rod-shaped portion 6 such that the angle 22 between the longitudinal axis of the rod-shaped portion 6 and the first sealing member 2, i.e. the line 20 is 0°. The first sealing member 2 is in a compressed state. Thereafter, the positioning device is pushed until the first sealing member 2 is conveyed out of the introducer 24 and is carried forward about one to five cm in front of the proximal end of the introducer 24. This because of that the user of the introducer 24 do not know the exactly length of the introducer 24 and if the introducer 24 is pulled out of the vessel 30 without the first sealing member 2 being set free and being expanded, the first sealing member 2 will be deposited on the outside of the vessel 30.

Figure 11:
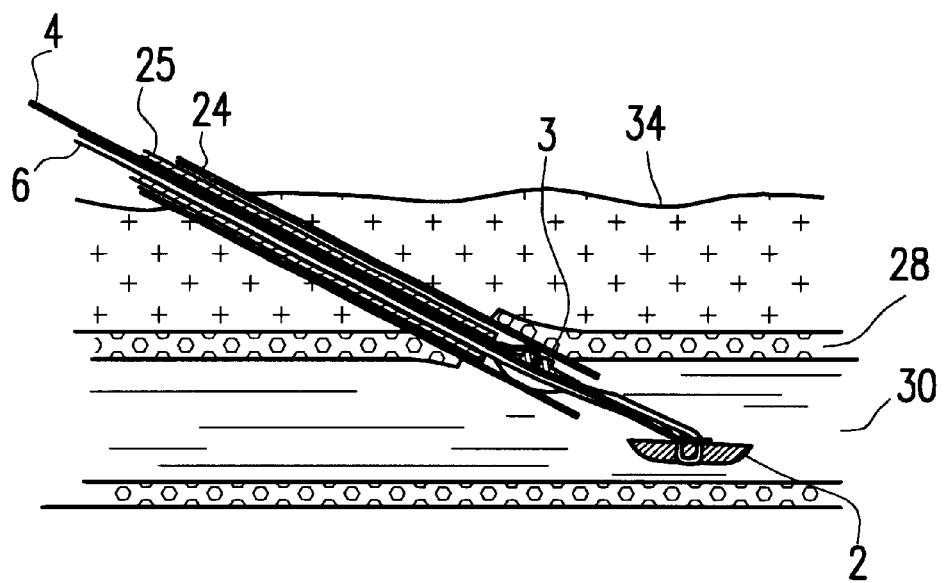
FIG. 11 shows a sectional view of the incision site wherein the first sealing member extends outside of the introducer and into the vessel.
Figure 12:
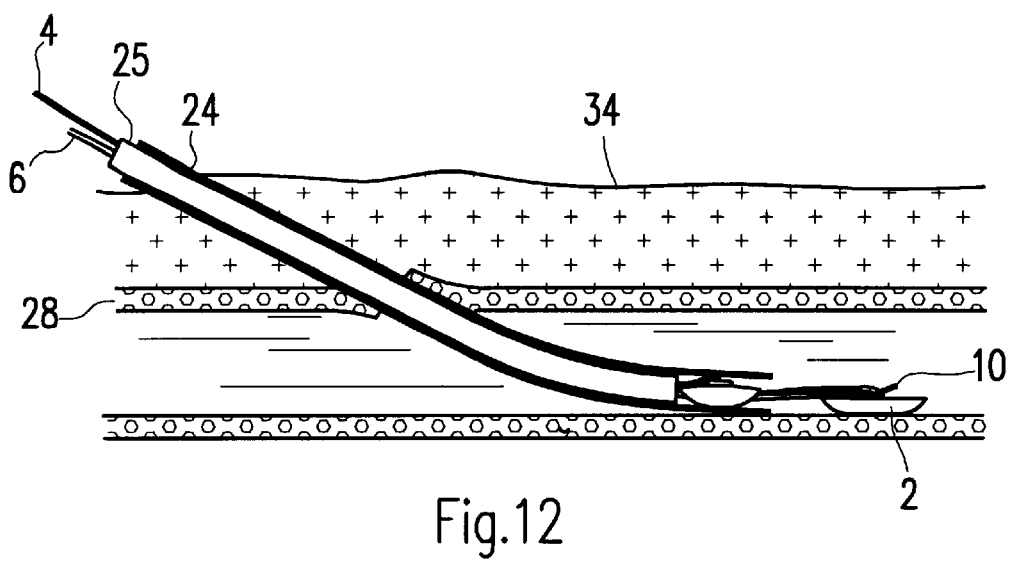
FIG. 12 shows a sectional view of the incision site wherein the first sealing member extends outside of the introducer and into the vessel and wherein the introducer is bent.

The first sealing member 2 has now reached the state as shown in FIG. 11 where the first sealing member 2 is pivoted towards the rod-shaped portion 6 such that the angle 22 between the longitudinal axis of the rod-shaped portion 6 and the first sealing member 2, i.e. the line 20 is the desired angle 22, or as shown in FIG. 12 wherein the introducer 24 is bent and the angle 22 between the longitudinal axis of the rod-shaped portion 6 and the first sealing member 2, i.e. the line 20, is 0°, preferably between approximately 15–30°. In this state the first sealing member 2 extends outside of the introducer 24 and into the vessel 30. As soon as the first sealing member 2 is outside of the introducer 24 it will unfold to an expanded state. Since the elongated portion 6 of the positioning device is fastened to the first sealing member 2, the first sealing member 2 cannot be moved off by the blood flow.

The position of the first sealing member 2 is now controllable by the user that moves the positioning device such that a movement of the rod-shaped portion 6 is transferable to the first sealing member 2. The position of the first sealing member 2 is controlled by rotation, by direction and by length of extension outside the introducer 24. It is desirable that the first sealing member 2 can be deposited and positioned without getting stuck or cause injury of the vessel.

This is possible when the first sealing member 2 is positioned in line with the vessel 30.

When the first sealing member 2 is brought to its right position to be sealed, the positioning device is to be removed.

The proximal end of the elongated member is unfastened from the support 12 so that the pressure that pressures the rod-shaped portion 6 against the first sealing member 2 ceases.

Figure 13:
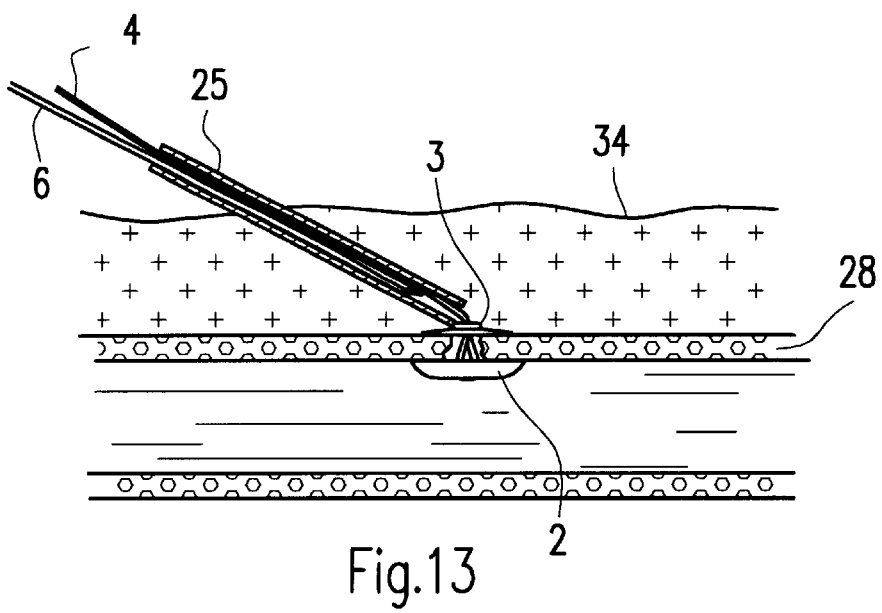
FIG. 13 shows a sectional view of the incision site wherein the rod-shaped portion is released from the first sealing member and pulled out through the introducer.

The rod-shaped portion 6 is then released from the first sealing member 2 and pulled out through the introducer 24. See FIG. 13.

Figure 14:
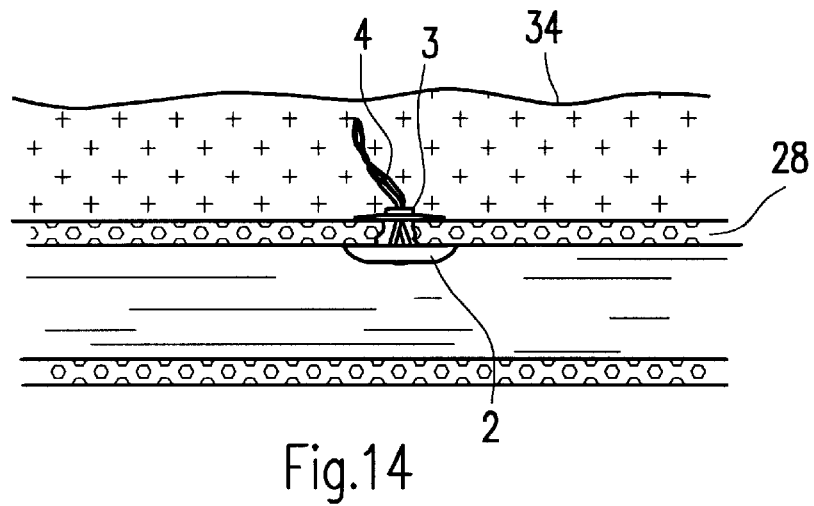
FIG. 14 shows a sectional view of the incision site wherein a tampering tube pushes the second sealing member into its final position.

FIG. 14 shows the next state, wherein the tampering tube 25 pushes the second sealing member 3 along the elongated member into its final position. Thereafter the tampering tube 25 and the introducer 24 are removed and the sealing device closes the incision.

It shall be noted that the different features depicted in the figures are not drawn in scale. The purpose of the figures is not to limit the invention to the dimensions or relations shown, but instead make it easy to understand the principles of the present invention.

Whilst this invention has been described in terms of preferred embodiments thereof, it will be appreciated that other forms could readily be adapted by one skilled in the art.

Accordingly, the scope of this invention is to be considered limited only by the following claims and equivalents thereof.

What is claimed is:

1. A positioning device for positioning a sealing device when closing an incision in a wall of a vessel, said sealing device comprising a first sealing member (2) attached to the distal end of an elongated member, characterised in that said positioning device comprises a rod-shaped portion (6) which in its distal end, is releasably attachable to said first sealing member (2) such that a rotational movement and a directional movement of the rod-shaped portion (6) is transferable to the first sealing member (2) to control the position of said first sealing member (2).

2. Positioning device according to claim 1, wherein the elongated member constitutes a pair of suture wires (4).

3. Positioning device according to claim 1, wherein the angle (22) between the longitudinal axis of the rod-shaped portion (6) and the longitudinal axis of the first sealing member (2), is between 0° and a desired angle of a magnitude such that, when the first sealing member (2) is in a position being deposited from an introducer (24) into the vessel (30), the line (20) is approximately parallel to the vessel.

4. Positioning device according to claim 3, wherein said desired angle is between zero and 30°.

5. Positioning device according to claim 3, wherein the first sealing member is adapted to be attached to be pivotable between the angle zero and said desired angle.

6. Positioning device according to claim 5, wherein the first sealing member (2) is pivotable between the angles zero and 30°.

7. Positioning device according to claim 1, wherein the rod-shaped portion (6) in its distal end fits in to a notch (7) within said first sealing member (2).

8. Positioning device according to claim 7, wherein the notch (7) in the first sealing member (2) is angled such that when the rod-shaped portion (6) is placed into the notch (7), the desired angle is provided.

9. Positioning device according to claim 1, wherein the rod-shaped portion (6) in its distal end comprises a shoulder (8) on each side of a projecting part (10) so that the rod-shaped portion (6) fits in between the first sealing member (2) and said pair of suture wires, where they extend from the first sealing member (2).

10. Positioning device according to claim 9, wherein the projecting part (10) is bent such that when attached to the first sealing member (2) the desired angle is provided.

11. Positioning device according to claim 1, wherein the rod-shaped portion (6) in its distal end comprises at least two projecting parts (40, 42) and a space (44) in-between said parts, forming a fork being adapted to surround the elongated member where it extends from the first sealing member (2).

12. Positioning device according to claim 11, wherein the at least two projecting parts (40, 42)) are bent such that when attached to the first sealing member (2) the desired angle is provided.

13. Positioning device according to claim 12, wherein the tips of the bent two projecting parts (40, 42) are further bent such that the distal end of the rod-shaped portion (6) is S-shaped.

14. Positioning device according to claim 1, wherein the rod-shaped portion (6) is tubular and has a first opening (50) in its distal end and a second opening (52) in its proximal end, such that the elongated member is threadable through the tube formed rod-shaped portion (6).

15. Positioning device according to claim 14, wherein the opening (50) of the tubular rod-shaped portion (6) is slanted in the same angle as the desired angle.

16. Positioning device according to claim 15, wherein a part of the tube formed rod-shaped portion (6) comprises a longitudinal slit (54) extending from the first opening (50).

17. Positioning device according to claim 16, wherein the slit (54) is terminated in a first opening (56) and wherein the slit further includes a second opening (58) between the first opening (56) and the distal end.

18. Positioning device according to claim 1, wherein the rod-shaped portion (6) is adapted to be kept in place to the first sealing member (2) by the elongated member.

19. Positioning device according to claim 18, wherein the proximal end of the elongated member is fastenable to the proximal end of the rod-shaped portion (6) so as to keep the rod-shaped portion (6) attached to the first sealing member (2).

20. Positioning device according to claim 19, wherein the positioning device comprises a support (12), which support (12) is attached to or is a part of the proximal end of the rod-shaped portion (6).

21. Positioning device according to claim 20, wherein the support (12) comprises a through opening (60) through which the elongated member, extending from the proximal end of the tube formed rod-shaped portion (6), is threadable.

22. Positioning device according to claim 21, wherein the proximal end of the elongated member adapted to be fastened to the support (12), in order to achieve a pressure that pressures the rod-shaped portion (6) against the first sealing member (2) so as to keep them together.

23. Incision closer device characterised in that it comprises a positioning device according to claim 1, and a sealing device for closing an incision in a wall of a vessel, which sealing device comprises a first sealing member (2) attached to a distal end of an elongated member and a second sealing member (3) which is threadable onto and along the elongated member (4) and is lockable in its final position for closing the incision.

* * * * *